US011298434B2

(12) United States Patent
Isola et al.

(10) Patent No.: US 11,298,434 B2
(45) Date of Patent: Apr. 12, 2022

(54) ULTRASONIC MEDICAL PROBE WITH FAILSAFE FOR STERILITY AND ASSOCIATED METHOD

(71) Applicant: MISONIX, INCORPORATED, Farmingdale, NY (US)

(72) Inventors: Scott Isola, Deer Park, NY (US); Alexander Darian, Brightwaters, NY (US); Dan Voic, Cedar Grove, NJ (US); Ronald Manna, Valley Stream, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 626 days.

(21) Appl. No.: 14/795,667

(22) Filed: Jul. 9, 2015

(65) Prior Publication Data

US 2017/0007852 A1  Jan. 12, 2017

(51) Int. Cl.
*A61L 2/07* (2006.01)
*A61B 17/32* (2006.01)
*A61B 90/00* (2016.01)

(52) U.S. Cl.
CPC ....... *A61L 2/07* (2013.01); *A61B 2017/32007* (2017.08); *A61B 2090/0807* (2016.02); *A61B 2090/0814* (2016.02)

(58) Field of Classification Search
CPC .............................................. A61B 2090/0814
See application file for complete search history.

(56) References Cited

U.S. PATENT DOCUMENTS

| 5,989,275 | A | * | 11/1999 | Estabrook | ........ A61B 17/22012 604/22 |
|---|---|---|---|---|---|
| 8,109,925 | B2 | | 2/2012 | Voic et al. | |
| 8,790,359 | B2 | | 7/2014 | Rabiner | |
| 9,440,292 | B1 | * | 9/2016 | Feinberg | ................... B23B 5/16 |
| 9,737,735 | B2 | | 8/2017 | Dietz et al. | |
| 10,973,537 | B2 | | 4/2021 | Mikus et al. | |

(Continued)

FOREIGN PATENT DOCUMENTS

| WO | WO98/37819 A1 | 9/1998 |
| WO | WO01/35812 A2 | 5/2001 |

OTHER PUBLICATIONS

McKeen, Laurence W. Plastics Used in Medical Devices. Handbk of Polymer Applications in Medicine and Medical Devices. Dec. 10, 2013, 1st edition, p. 39.

(Continued)

*Primary Examiner* — Jason M Ip
(74) *Attorney, Agent, or Firm* — R. Neilsudol; Henry D. Coleman

(57) ABSTRACT

An ultrasonic medical probe has a horn or shaft, a shank at a proximal end of the shaft, a probe head at a distal end of the horn or shaft, opposite the shank, and at least one polymeric component fixed to at least one of the horn or shaft, the shank, and the probe head. The shank is provided at a proximal end opposite the horn or shaft with an externally threaded connector for attaching the probe to a source of ultrasonic vibratory energy. The polymeric component is of a composition that transmits and is essentially impervious to ultrasonic vibratory energy but that degrades or decomposes upon exposure to a source of extreme energy (other than ultrasonic vibratory energy), rendering the probe inoperative for use.

10 Claims, 4 Drawing Sheets

(56) References Cited

U.S. PATENT DOCUMENTS

2007/0215001 A1   9/2007   Voegele
2014/0200580 A1   7/2014   Joseph
2015/0088137 A1   3/2015   Manna

OTHER PUBLICATIONS

Takenaga, Kyle, Ultrasonic Physics-101, https://www.probomedical.com/blog/ultrasound-physics-101/; May 17, 2017.

* cited by examiner

ULTRASONIC MEDICAL PROBE WITH FAILSAFE FOR STERILITY AND ASSOCIATED METHOD

BACKGROUND OF THE INVENTION

This invention relates to an ultrasonic medical tool or probe. More particularly, this invention relates to such a tool or probe with one or more failsafe components for ensuring sterile use of the tool or probe. This invention also relates to an associated medical method.

It is well known that hospitals routinely subject medical instruments, particularly surgical instruments, to sterilization procedures such as autoclaving, in order to enable or justify re-use of the instruments. It is not so well known that autoclaving and other sterilization procedures are far from effective in ensuring sterility. Many patients, particularly those undergoing invasive surgical procedures are subject to risk from improperly or incompletely sterilized instruments.

The problem of sterilizing surgical instruments is particularly difficult when the instruments are elongate probes that are provided with a narrow channel or lumen, for instance, for irrigation or suction purposes. Elongate flexible endoscopes, such as those used in colonoscopic investigations and treatments have channels or lumens for the insertion of endoscopic instruments. It is not uncommon for organic debris from a patient to be come lodged in the channel or lumen. Such particulate matter deep inside the channel or lumen is naturally resistant or impervious to autoclaving procedures.

It is of further note that medical tools subjected to repeated extremes of heat or other forms of bactericidal energy may drift away from their optimal performance specifications. Unbeknownst to the users of sterilized ultrasonic medical instrumentation, the instruments may depart from optimal performance so that effectiveness is impacted.

OBJECTS OF THE INVENTION

It is an object of the present invention to provide improved medical instruments, wherein sterility is guaranteed. More particularly, the present invention seeks to provide surgical instruments, particularly ultrasonic probes, that are usable only in a completely sterile condition.

A related object of the present invention is to provide a medical instrument, particularly including an ultrasonic probe, with means for enabling detection that the instrument or probe has been subjected to a sterilization procedure.

It is another object of the present invention to provide an associated method for ensuring sterility of instrumentation used in invasive medical procedures.

A related object of the present invention is to provide an ultrasonic medical instrument with means for preventing or reducing potential ineffectiveness and undesirable effects on organic tissues were the instrument to be used in a suboptimal condition.

A more particular object of the present invention is to provide an ultrasonic medical instrument with such means that are easy to detect by medical personnel.

These and other objects of the present invention will be apparent from the descriptions and drawings herein. Although every object of the invention is attainable by at least one embodiment of the invention, there is not necessarily any single embodiment that achieves all of the objects of the invention.

SUMMARY OF THE INVENTION

An ultrasonic medical probe comprises, in accordance with the present invention, a horn or shaft, a shank at a proximal end of the shaft, a probe head at a distal end of the horn or shaft, opposite the shank, and at least one polymeric component fixed to at least one of the horn or shaft, the shank, and the probe head. The shank is provided at a proximal end opposite the horn or shaft with an externally threaded connector for attaching the probe to a source of ultrasonic vibratory energy. The shank typically includes a pair of opposed flats, which are engageable with a wrench for tightly fixing the shank to the source of ultrasonic vibratory energy. The polymeric component is of a composition that transmits and is essentially impervious to ultrasonic vibratory energy but that degrades or decomposes upon exposure to a source of extreme energy (other than ultrasonic vibratory energy), rendering the probe inoperative for use.

The extreme energy may be heat energy applied upon a disposition of a used probe in an autoclave. The polymeric or plastic component will at least partially melt, to a extent that is readily detectable by (e.g., visible to) a user.

The polymeric component may be a plug or insert lodged in a recess along an external surface of the horn or shaft. For instance, the polymeric component may have the shape of an annulus or a ring. The annulus or ring has an outer diameter equal to an outer diameter of the horn or shaft adjacent the recess so as to provide the horn or shaft with a smooth and continuous outer surface. After autoclaving of the probe and a consequent disintegration or melting of the polymeric annulus, the horn or shaft has a ring-shaped recess. The reduced diameter of the horn or shaft at the recess would cause the probe to snap or bend at the recess. This weakness would be apparent to a prospective user or re-user.

Where the probe is formed with a longitudinal channel or bore (e.g., for irrigation and/or suction), an at least partially transverse hole may be formed in the shank or horn, which communicates with the channel or bore proximally of the probe head. In this case, the polymeric component takes the form of a plug or insert filling the hole. Upon autoclaving of the probe and a consequent disintegration or melting of the polymeric plug, connecting of the probe to a handle and connecting of the channel or bore to a source of pressurized irrigation fluid results in a marked leakage or spraying of the irrigation fluid from the transverse hole vacated by the polymeric component.

Where the polymeric component is provided on the shank formed with one or both of the flats, autoclaving of the probe and a consequent disintegration or melting of the polymeric component removes the flats and makes it difficult if not impossible to effectively connect the probe to an electromechanical transducer such as a stack of piezoelectric crystals or a magnetostrictive converter.

Where the polymeric component forms at least a portion of the externally threaded connector, autoclaving of the probe and a consequent disintegration or melting of the polymeric component removes or degrades the connector at least in part and accordingly makes it difficult if not impossible to effectively connect the probe to an electromechanical transducer such as a stack of piezoelectric crystals or a magnetostrictive converter.

Other kinds of polymeric inserts or component parts may occur to one skilled in the art based on the above exemplary embodiments. The invention contemplates providing an ultrasonic probe or other surgical instrument with a part that is destroyed by the sterilization process, so that the probe cannot be used again in another surgical or invasive medical procedure and so that the damage to the probe or instrument is readily apparent and easily detectible .

A medical method in accordance with the present invention comprises providing an ultrasonic probe incorporating at least one polymeric component, generating an ultrasonic standing wave in the probe, placing an operative surface at a distal end of the probe into contact with a tissue surface of a patient, conducting vibratory energy through the probe into tissue of the patient by virtue of the generating of the standing wave and the placing of the operative surface, and subsequently subjecting the probe to extreme energy, causing degradation or decomposition of the at least one polymeric component.

Typically, subjecting the probe to extreme energy includes placing the probe in an autoclave and subsequently operating the autoclave. However, the invention contemplates that the polymeric material of the probe or instrument may degrade or deform in response to other forms of sterilizing or bactericidal energy, such as ultraviolet radiation or alcohol solution.

The method may further comprise discarding the probe or instrument with the degraded or decomposed polymeric component, without further use. The discarding may including recycling, whereby the instrument may be thoroughly sterilized and refurbished, together with one or more new polymeric components.

The present invention also serves to ensure optimal tool efficacy in every case. Because the operational characteristics of the probes may be subject to change through repeated autoclaving so that the can probes no longer function at design specifications, the present invention assures optimal structural and operational characteristics in each operation.

DETAILED DESCRIPTION

Figure 1:
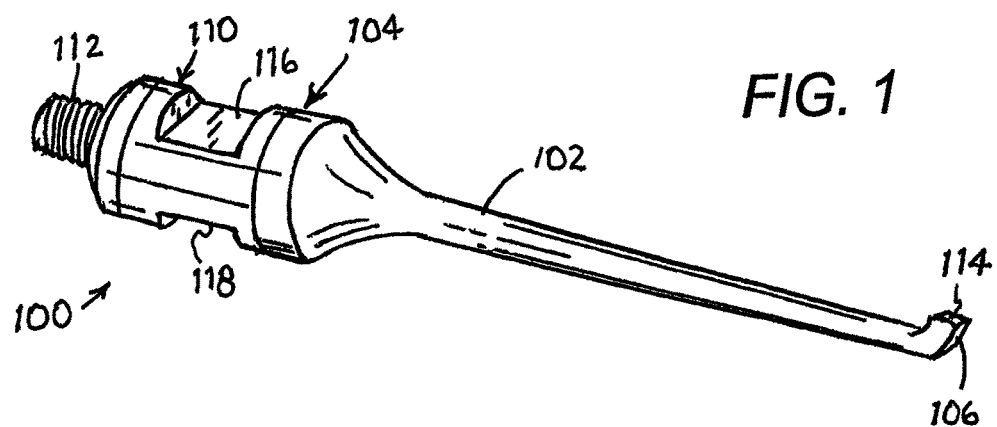
FIG. 1 is a schematic perspective view of an ultrasonic probe in accordance with the present invention, showing the probe before a sterilization procedure.

As depicted in FIG. 1, an ultrasonic medical probe 100 with a re-use failsafe structure includes a horn or shaft 102, a shank 104 at a proximal end of the shaft 102, an eccentric probe head 106 at a distal end of the horn or shaft 102, opposite the shank 104, and a polymeric component 110 fixed to and incorporated into the shank 104. Shank 104 is provided at a proximal end opposite the horn or shaft 102 with an externally threaded connector 112 for attaching the probe 100 to a source of ultrasonic vibratory energy. Typically, the probe 100 is connected, prior to use of the instrument in a surgical procedure, to a piezoelectric crystalline transducer stack housed in a handle. The transducer stack or array is electrically connectable to a generator of an alternating waveform of a predetermined ultrasonic frequency so as to generate an ultrasonic standing wave in probe 100. Probe head 106 has an operative or effector surface 114 that is placed into contact with organic tissues of a patient for conducting ultrasonic vibratory energy into the tissues during operation of the device.

Figure 2:
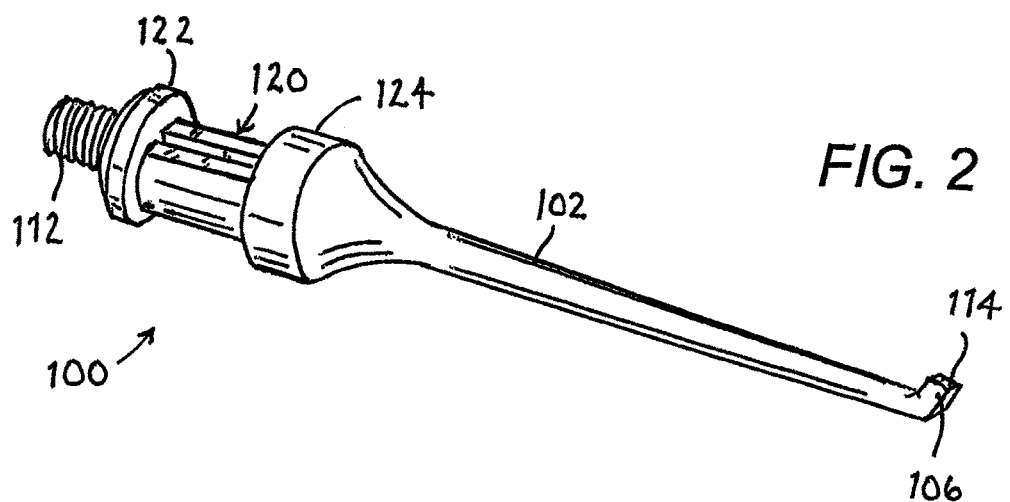
FIG. 2 is a schematic perspective view of the ultrasonic probe of FIG. 1, showing the probe after a sterilization procedure.

Shank 104 typically includes a pair of opposed flats 116 and 118, which are engageable by a wrench for tightly fixing the shank to the source of ultrasonic vibratory energy, that is, the piezoelectric transducer. In the probe of FIG. 1, the flats 116 and 118 are provided on polymeric component 110, which extends around a midsection of shank 104. Polymeric component 110 is of a composition that transmits and is essentially impervious to ultrasonic vibratory energy but that degrades or decomposes upon exposure to a source of extreme energy (other than ultrasonic vibratory energy), rendering the probe inoperative for use. In particular, the material of polymeric component 110 decomposes, disintegrates or melts upon exposure to extreme heat in an autoclave. The polymeric or plastic component will at least partially melt, to a extent that is readily detectable by (e.g., visible to) a user. FIG. 2 shows the probe 100 after polymeric component 110 has melted completely away. Shank 104 is visibly transformed and has such a different appearance as to readily signal that it is no longer utilizable. Shank 104 includes one or more core members 120 extending between a proximal end segment 122 carrying threaded connector 112 and a distal end segment 124 from which horn or shaft 102 projects.

Figure 3:
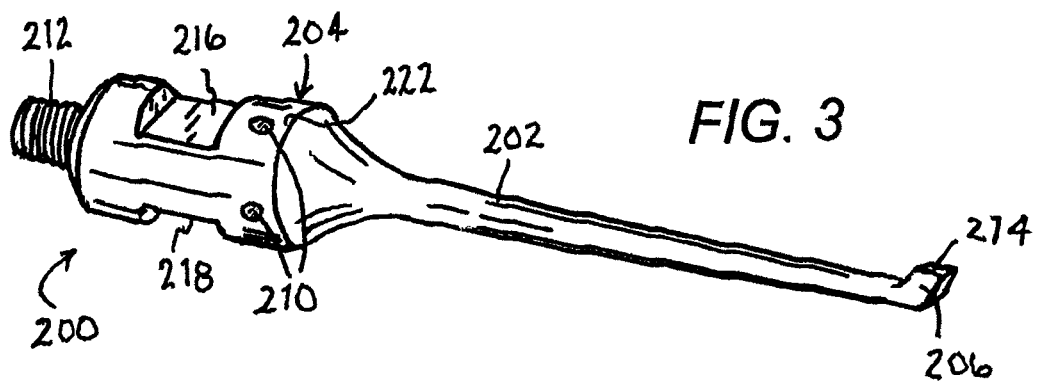
FIG. 3 is a schematic perspective view of another embodiment of an ultrasonic probe in accordance with the present invention, showing the probe before a sterilization procedure.
Figure 4:
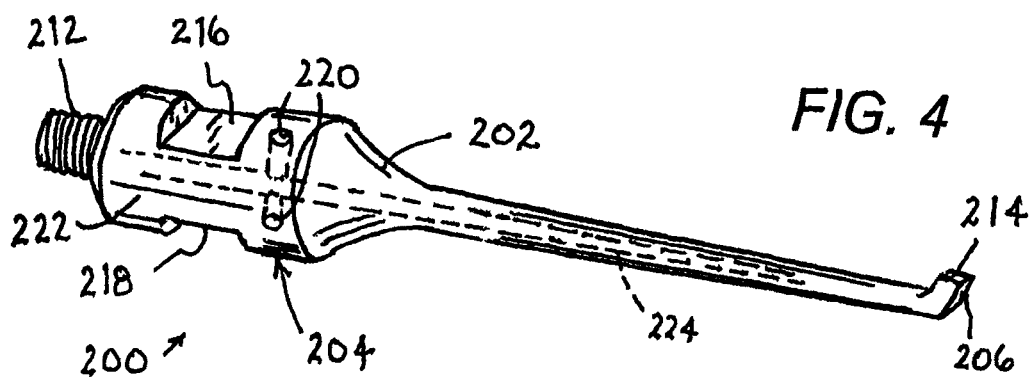
FIG. 4 is a schematic perspective view of the ultrasonic probe of FIG. 3, showing the probe after a sterilization procedure.

As illustrated in FIGS. 3 and 4, an ultrasonic medical probe 200 with a re-use failsafe structure includes a horn or shaft 202, a shank 204 at a proximal end of the shaft 202, an eccentric probe head 206 at a distal end of the horn or shaft 202, opposite the shank 204, and a plurality of polymeric plugs 210 inserted or disposed in respective holes 220 in the shank 204. Shank 204 is provided at a proximal end opposite the horn or shaft 202 with an externally threaded connector 212 for attaching the probe 200 to a source of ultrasonic vibratory energy. Typically, the probe 200 is connected, prior to use of the instrument in a surgical procedure, to a piezoelectric crystalline transducer stack housed in a handle. The transducer stack or array is electrically connectable to a generator of an alternating waveform of a predetermined ultrasonic frequency so as to generate an ultrasonic standing wave in probe 200. Probe head 206 has an operative or effector surface 214 that is placed into contact with organic tissues of a patient for conducting ultrasonic vibratory energy into the tissues during operation of the device.

Shank 204 includes a pair of opposed flats 216 and 218, which are engageable by a wrench for tightly fixing the shank to the source of ultrasonic vibratory energy, that is, the piezoelectric transducer.

The polymeric or thermoplastic material of plugs 210 transmits ultrasonic vibratory energy but degrades or decomposes upon exposure to a source of extreme energy (other than ultrasonic vibratory energy), rendering probe 200 inoperative for use. In particular, the material of polymeric plugs 210 decomposes, disintegrates or melts upon exposure to extreme heat in an autoclave. Plugs 210 will at least partially melt, to a extent that is readily detectable by (e.g., visible to) a user. FIG. 3 shows outer surfaces (not separately designated) of polymeric plugs 210 at least approximately continuous with a cylindrical outer surface 222 of shank 204, while FIG. 4 shows probe 200 after polymeric plugs 210 have melted completely away. Shank 204 is transformed so that holes 220 are visible. Moreover, probe 200 (like probe 100) is typically provided with a central channel or bore 224 for the conduction of irrigation liquid to probe head 206 and out through an opening (not shown) in operative or effector surface 214. Holes 220 may communicate with channel or bore 224 so that liquid will exit shank 204 through holes 220 after plugs 210 are removed by autoclaving or the application of another form of extreme energy and upon connecting of channel or bore 224 to a supply of pressurized irrigation fluid.

Figure 5:
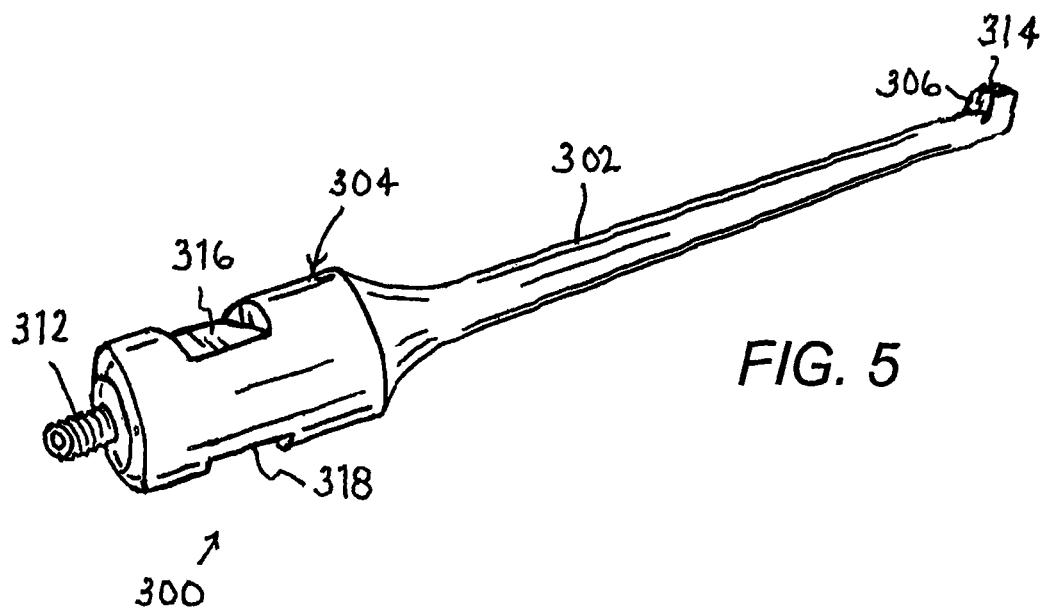
FIG. 5 is a schematic perspective view of a further ultrasonic probe in accordance with the present invention, showing the probe before a sterilization procedure.

As shown in FIG. 5, another ultrasonic medical probe 300 with a re-use failsafe structure includes a horn or shaft 302, a shank 304 at a proximal end of the shaft 302, an eccentric probe head 306 at a distal end of the horn or shaft 302, opposite the shank 304. Shank 304 is provided at a proximal end opposite the horn or shaft 302 with an externally threaded connector 312 for attaching the probe 100 to a source of ultrasonic vibratory energy. Typically, prior to use of the instrument in a surgical procedure, the probe 300 is coupled via connector 312 to a piezoelectric crystalline transducer stack housed in a handle. The transducer stack or array is electrically connectable to a generator of an alternating waveform of a predetermined ultrasonic frequency so as to generate an ultrasonic standing wave in probe 300. Probe head 306 has an operative or effector surface 314 that is placed into contact with organic tissues of a patient for conducting ultrasonic vibratory energy into the tissues during operation of the device.

Figure 6:
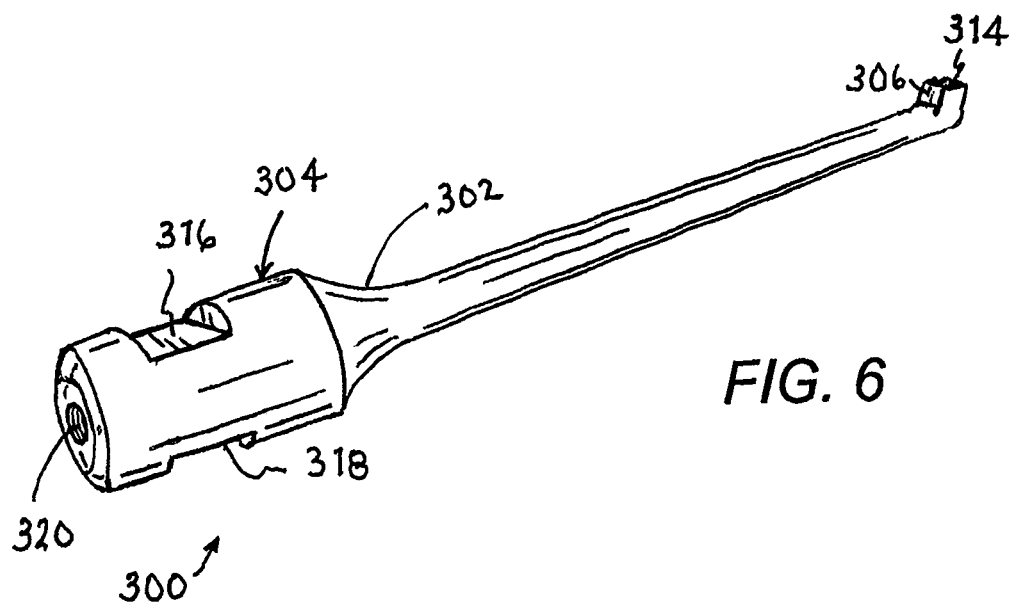
FIG. 6 is a schematic perspective view of the ultrasonic probe of FIG. 5, showing the probe after a sterilization procedure.

Shank 304 includes a pair of opposed flats 316 and 318, which are engageable by a wrench for tightly fixing the shank to the source of ultrasonic vibratory energy, that is, the piezoelectric transducer. In the probe of FIG. 5, connector 312 is made of a hard polymeric or thermoplastic material that transmits and is essentially impervious to ultrasonic vibratory energy but that degrades or decomposes upon exposure to a source of extreme energy (other than ultrasonic vibratory energy), rendering the probe inoperative for use. In particular, the material of polymeric connector 312 decomposes, disintegrates or melts upon exposure to extreme heat in an autoclave. Connector 312 will at least partially melt, to a extent that is not only readily detectable by (e.g., visible to) a user but that renders the probe 300 incapable of connection to a transducer array, such as that conventionally disposed in an instrument handle or medical handpiece. FIG. 6 shows the probe 300 after polymeric connector 312 has melted completely away, rendering visible an internally threaded bore 320 in shank 304. Thus shank 304 is visibly transformed and has such a different appearance as to readily signal that probe 300 is no longer utilizable.

Figure 7:
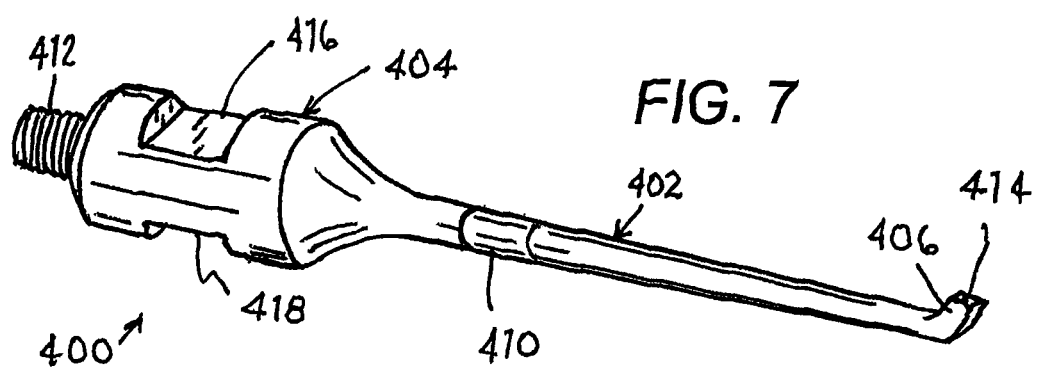
FIG. 7 is a schematic perspective view of yet another ultrasonic probe in accordance with the present invention, showing the probe before a sterilization procedure.

FIG. 7 depicts a further ultrasonic medical probe 400 with a re-use failsafe structure. Probe 400 includes a horn or shaft 402, a shank 404 at a proximal end of the horn 402, an eccentric probe head 406 at a distal end of the horn or shaft 402, opposite the shank 404, and a polymeric component 410 fixed to and incorporated into the horn 402. Shank 404 is provided at a proximal end opposite the horn 402 with an externally threaded connector 412 for attaching the probe 400 to a source of ultrasonic vibratory energy. Probe 400 is connected, prior to use of the instrument in a surgical procedure, to a piezoelectric crystalline transducer stack housed in an instrument handle. The transducer stack or array is electrically connectable to a generator of an alternating waveform of a predetermined ultrasonic frequency so as to generate an ultrasonic standing wave in probe 400. Probe head 406 has an operative or effector surface 414 that is placed into contact with organic tissues of a patient for conducting ultrasonic vibratory energy into the tissues during operation of the device.

Shank 404 includes a pair of opposed flats 416 and 418, which are engageable by a wrench for tightly fixing the shank to the source of ultrasonic vibratory energy, that is, the piezoelectric transducer.

Figure 8:
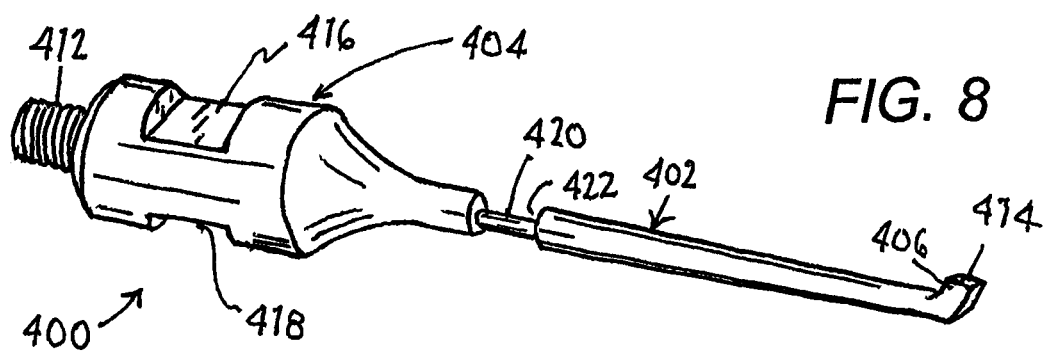
FIG. 8 is a schematic perspective view of the ultrasonic probe of FIG. 7, showing the probe after a sterilization procedure.

The polymeric or thermoplastic material of component 410 transmits and is essentially impervious to ultrasonic vibratory energy but degrades or decomposes upon exposure to a source of extreme energy (other than ultrasonic vibratory energy), rendering the probe inoperative for use. In particular, the material of polymeric component 410 decomposes, disintegrates or melts upon exposure to extreme heat in an autoclave. The polymeric or plastic component 410 will at least partially melt, to a extent that is readily detectable by (e.g., visible to) a user. FIG. 8 shows the probe 400 after polymeric component 410 has melted completely away to expose a reduced diameter section 420 of horn 402.

In the embodiment of FIGS. 7 and 8, polymeric component 410 has an annular or ring-shaped form and is disposed in an annular recess 422 in horn 402. Horn 402 is visibly transformed and has such a different appearance after the decomposition of polymeric annulus or ring 410 as to readily signal that probe 400 is no longer utilizable. Indeed, the probe horn 402 would likely snap or bend under applied forces, were one to attempt to use the autoclaved instrument in a further surgical procedure, This weakness or susceptibility of the probe 400 would be readily apparent.

Prior to heat treatment in an autoclave, polymeric annulus or ring 410 has an outer diameter equal to an outer diameter of the horn or shaft 402 adjacent recess 422 so as to provide the horn or shaft with a smooth and continuous outer surface.

Other kinds of polymeric inserts or component parts may occur to one skilled in the art based on the above exemplary embodiments. The invention contemplates providing an ultrasonic probe or other surgical instrument with a part that is destroyed by the sterilization process, so that the probe cannot be used again in another surgical or invasive medical procedure and so that the damage to the probe or instrument is readily apparent and easily detectable.

A medical method utilizing probe 100, 200, 300 or 400 includes generating an ultrasonic standing wave in the probe, placing operative surface 114, 214, 314, or 414 into contact with a tissue surface of a patient, conducting vibratory energy through the probe 100, 200, 300, 400 into tissue of the patient by virtue of the generating of the standing wave and the placing of the operative surface, and subsequently subjecting the probe to extreme energy, causing degradation or decomposition of the respective polymeric component 110, 210, 312, 410.

Typically, subjecting the probe 100, 200, 300 or 400 to extreme energy includes placing the probe in an autoclave and subsequently operating the autoclave. However, the invention contemplates that the polymeric material of the probe or instrument may degrade or deform in response to other forms of sterilizing or bactericidal energy, such as ultraviolet radiation or alcohol solution.

The method may further comprise discarding the probe or instrument with the degraded or decomposed polymeric component, without further use. The discarding may including recycling, whereby the instrument may be thoroughly sterilized and refurbished, together with one or more new polymeric components.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic medical probe comprising:
   a horn or shaft;
   a probe head at a distal end of said horn or shaft;
   a shank at a proximal end of said shaft opposite said probe head, said shank including a pair of opposed flats, said shank being provided at a proximal end opposite said horn or shaft with an externally threaded connector configured for attaching the probe to a source of ultrasonic vibratory energy so as to enable generation of a standing wave in said horn or shaft, said shank and said probe head and a transmission of ultrasonic vibratory energy into target tissues of a patient via an operative surface of said probe head; and
   at least one polymeric component mounted to at least one of said horn or shaft, said shank, and said probe head,
   said at least one polymeric component being disposed in a recess in said at least one of said horn or shaft, said shank, and said probe head,
   said at least one polymeric component being of a composition that is impervious to ultrasonic vibratory energy and that degrades or decomposes upon exposure to a source of energy other than ultrasonic vibratory energy, rendering the probe inoperative for use.

2. The ultrasonic medical probe defined in claim 1 wherein said at least one polymeric component is provided in a recess along an external surface of said horn or shaft.

3. The ultrasonic medical probe defined in claim 2 wherein said at least one polymeric component is an annular or ring shaped part having an outer diameter equal to an outer diameter of said horn or shaft at said recess.

4. The ultrasonic medical probe defined in claim 1 wherein said probe is provided with a longitudinal channel or bore and an at least partially transverse hole communicating with said channel or bore proximally of said probe head, said at least one polymeric component being disposed in said hole, filling said hole.

5. The ultrasonic medical probe defined in claim 1 wherein said at least one polymeric component is provided on said shank and is formed with one of said flats.

6. The ultrasonic medical probe defined in claim 1 wherein said at least one polymeric component forms at least a portion of said externally threaded connector.

7. A medical method comprising:
   providing an ultrasonic probe including:
   a horn or shaft;
   a shank at a proximal end of said horn or shaft, said shank including a pair of opposed flats, said shank being provided at a proximal end opposite said horn or shaft with an externally threaded connector for attaching the probe to a source of ultrasonic vibratory energy; and
   a probe head at a distal end of said horn or shaft, opposite said shank,
   said probe incorporating at least one polymeric component, said at least one polymeric component being disposed in a recess in at least one of said horn or shaft, said shank and said probe head;
   operatively connecting said probe to said source of ultrasonic vibratory energy via said externally threaded connector;
   generating an ultrasonic standing wave in said probe including said horn or shaft, said shank and said probe head;
   placing an operative surface on said probe head into contact with a tissue surface of a patient;
   by virtue of the generating of said standing wave in said probe including said horn or shaft, said shank and said probe head and the placing of said operative surface, conducting vibratory energy through said probe including said horn or shaft, said shank, said probe head and said operative surface into tissue of the patient; and
   subsequently subjecting said probe to energy causing degradation or decomposition of said at least one polymeric component.

8. The method defined in claim 7 wherein the subjecting of said probe to energy includes placing said probe in an autoclave and subsequently operating said autoclave.

9. The method defined in claim 7, further comprising discarding the probe with the degraded or decomposed polymeric component, without further use.

10. The ultrasonic medical probe defined in claim 5 wherein said shank includes a plurality of core members extending between the proximal end of said shank and a distal end of said shank, said at least one polymeric component being formed over said plurality of core members.

* * * * *